United States Patent
Suarez del Real Pena et al.

(10) Patent No.: US 11,255,844 B2
(45) Date of Patent: Feb. 22, 2022

(54) PERITONEAL DIALYSIS SYSTEMS AND RELATED METHODS

(71) Applicant: Fresenius Medical Care Holdings, Inc., Waltham, MA (US)

(72) Inventors: Diego Suarez del Real Pena, Mission, TX (US); Irving Hernandez, Rio Bravo (MX)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 429 days.

(21) Appl. No.: 15/912,874

(22) Filed: Mar. 6, 2018

(65) Prior Publication Data

US 2019/0277835 A1  Sep. 12, 2019

(51) Int. Cl.

| | |
|---|---|
| *G01N 33/52* | (2006.01) |
| *A61M 1/28* | (2006.01) |
| *A61B 5/00* | (2006.01) |
| *A61M 1/16* | (2006.01) |
| *G01N 33/84* | (2006.01) |
| *G01N 33/50* | (2006.01) |

(52) U.S. Cl.
CPC ........... *G01N 33/52* (2013.01); *A61B 5/6866* (2013.01); *A61M 1/1609* (2014.02); *A61M 1/28* (2013.01); *A61M 1/287* (2013.01); *G01N 33/5005* (2013.01); *G01N 33/84* (2013.01); *A61M 2202/0439* (2013.01); *A61M 2205/6081* (2013.01); *A61M 2205/702* (2013.01)

(58) Field of Classification Search
CPC .... G01N 33/52; G01N 33/5005; G01N 33/84; A61M 2202/0439; A61M 2205/6081; A61M 2205/702; A61M 1/1609; A61M 1/28; A61M 1/287; A61B 5/6866
USPC .......................................................... 604/29
See application file for complete search history.

(56) References Cited

U.S. PATENT DOCUMENTS

| | | |
|---|---|---|
| 4,654,298 A | 3/1987 | Babb et al. |
| 4,717,652 A | 1/1988 | Babb et al. |
| | (Continued) | |

FOREIGN PATENT DOCUMENTS

| | | |
|---|---|---|
| CN | 206526334 | 9/2017 |
| EP | 3281656 | 2/2018 |
| | (Continued) | |

OTHER PUBLICATIONS

Anonymous, "Point-of-care testing for peritoneal dialysis patients," Technology Networks, Retrieved from the Internet: URL<https://www.technologynetworks.com/diagnostics/blog/point-of-care-testing-for-peritoneal-dialysis-patients-290558> Retrieved on Apr. 5, 2019.
(Continued)

*Primary Examiner* — Brandy S Lee
*Assistant Examiner* — Nidah Hussain
(74) *Attorney, Agent, or Firm* — Fish & Richardson P.C.

(57) ABSTRACT

A peritoneal dialysis (PD) fluid line set includes a fluid line configured to carry spent dialysate to a drain receptacle and a chemical testing device disposed along the fluid line. The chemical testing device is configured to detect a presence of a substance in the spent dialysate as the spent dialysate flows past the chemical testing device, and the chemical testing device is configured to provide a visual indicator of the presence of the substance in the spent dialysate.

29 Claims, 11 Drawing Sheets

(56) References Cited

U.S. PATENT DOCUMENTS

| | | | |
|---|---|---|---|
| 4,717,658 A * | 1/1988 | Michaels | C07K 5/0808 435/18 |
| 6,605,447 B2 | 8/2003 | Weiss et al. | |
| 6,913,590 B2 | 7/2005 | Sorenson et al. | |
| 8,180,574 B2 | 5/2012 | Lo et al. | |
| 8,728,023 B2 | 5/2014 | Landherr et al. | |
| 8,777,891 B2 | 7/2014 | Landherr et al. | |
| 8,801,652 B2 | 8/2014 | Landherr et al. | |
| 8,945,936 B2 | 2/2015 | Ash et al. | |
| 9,381,289 B2 | 7/2016 | Hedmann et al. | |
| 9,440,017 B2 | 9/2016 | Rohde et al. | |
| 9,599,599 B2 | 3/2017 | Ash et al. | |
| 2002/0123715 A1 | 9/2002 | Sorenson et al. | |
| 2002/0164658 A1 | 11/2002 | Weiss et al. | |
| 2003/0216677 A1 | 11/2003 | Pan et al. | |
| 2005/0131340 A1 | 6/2005 | Sorenson et al. | |
| 2008/0045884 A1 | 2/2008 | Landherr et al. | |
| 2008/0183126 A1 | 7/2008 | Landherr et al. | |
| 2008/0183127 A1 | 7/2008 | Landherr et al. | |
| 2009/0149776 A1 | 6/2009 | Adams | |
| 2009/0299272 A1 * | 12/2009 | Hopping | A61M 1/28 604/29 |
| 2010/0005416 A1 | 1/2010 | Hedmann et al. | |
| 2010/0010101 A1 | 1/2010 | Cherukuri | |
| 2012/0052595 A1 * | 3/2012 | Wallace | G01N 33/558 436/501 |
| 2012/0258545 A1 | 10/2012 | Ash et al. | |
| 2013/0196311 A1 * | 8/2013 | Sambursky | G01N 33/526 435/5 |
| 2014/0276376 A1 | 9/2014 | Rohde et al. | |
| 2015/0204831 A1 | 7/2015 | Ash et al. | |
| 2015/0293115 A1 * | 10/2015 | Buhimschi | G01N 33/6839 436/86 |
| 2016/0375189 A1 | 12/2016 | Rohde et al. | |
| 2017/0281064 A1 | 10/2017 | Bayon | |
| 2018/0043078 A1 | 2/2018 | Gerber et al. | |
| 2018/0043080 A1 | 2/2018 | Gerber et al. | |
| 2018/0067106 A1 * | 3/2018 | Sim | G01N 33/521 |
| 2018/0356413 A1 * | 12/2018 | Parekh | C12Q 1/37 |
| 2018/0364224 A1 * | 12/2018 | Pulitzer | G01N 33/558 |

FOREIGN PATENT DOCUMENTS

| | | |
|---|---|---|
| WO | WO 2009/094034 | 7/2009 |
| WO | WO 2009/094035 | 7/2009 |
| WO | WO 2011/147425 | 12/2011 |
| WO | WO 2015/199534 | 12/2015 |
| WO | WO 2017/089801 | 6/2017 |
| WO | WO 2018/030354 | 2/2018 |
| WO | WO 2018/031711 | 2/2018 |

OTHER PUBLICATIONS

International Search Report and Written Opinion in Application No. PCT/US2019/014658, dated May 2, 2019, 12 pages.

Park et al., "Using reagent strips for rapid diagnosis of peritonitis in peritoneal dialysis patients," Advances in Peritoneal Dialysis 21:69-71, Jan. 1, 2005.

PCT International Preliminary Report on Patentability in International Application No. PCT/US2019/014658, dated Sep. 8, 2020, 9 pages.

* cited by examiner

PERITONEAL DIALYSIS SYSTEMS AND RELATED METHODS

TECHNICAL FIELD

This disclosure relates to peritoneal dialysis (PD) machines, and more particularly to testing effluent flowing through fluid lines of PD machines.

BACKGROUND

Dialysis is a treatment used to support a patient with insufficient renal function. The two principal dialysis methods are hemodialysis and peritoneal dialysis. During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), the patient's peritoneal cavity is periodically infused with dialysate. The membranous lining of the patient's peritoneum acts as a natural semi-permeable membrane that allows diffusion and osmosis exchanges to take place between the solution and the blood stream. These exchanges across the patient's peritoneum result in the removal of waste products, including solutes like urea and creatinine, from the blood, and regulate the levels of other substances, such as sodium and water, in the blood.

Automated PD machines called PD cyclers are designed to control the entire PD process so that it can be performed at home, usually overnight without clinical staff in attendance. This process is termed continuous cycler-assisted PD (CCPD). Many PD cyclers are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle. In some cases, spent dialysate (also referred to as effluent) that is removed from the patient's peritoneal cavity can be examined for indications of an infection of the peritoneum.

SUMMARY

This disclosure relates to testing effluent flowing through drain lines of peritoneal dialysis (PD) machines in order to facilitate early diagnosis of peritonitis.

In one aspect, a peritoneal dialysis (PD) fluid line set includes a fluid line configured to carry spent dialysate to a drain receptacle and a chemical testing device disposed along the fluid line. The chemical testing device is configured to detect a presence of a substance in the spent dialysate as the spent dialysate flows past the chemical testing device, and the chemical testing device is configured to provide a visual indicator of the presence of the substance in the spent dialysate.

Implementations may include one or more of the following features.

In some implementations, the chemical testing device includes a test pad that has an initial color and that includes one or more reagents that are reactive with the sub stance.

In some implementations, the chemical testing device further includes a control pad that lacks the one or more reagents and that has a reference color that is the same as the initial color of the test pad.

In some implementations, the test pad is configured such that the initial color changes with respect to the reference color upon contact between the substance and the one or more reagents.

In some implementations, the substance is a first substance, the test pad is a first test pad, the control pad is a first control pad, and the chemical testing device further includes a second test pad and a second control pad to detect a presence of a second substance in the spent dialysate as the spent dialysate flows past the chemical testing device.

In some implementations, the initial reference colors of the first test pad and the first control pad are different from initial reference colors of the second test pad and the second control pad, respectively.

In some implementations, the chemical testing device defines a fluid channel through which the spent dialysate can flow.

In some implementations, the chemical testing device includes a semi-permeable membrane that allows passage of the substance from the spent dialysate flowing in the fluid channel to the test pad.

In some implementations, the chemical testing device includes a lens through which the test pad can be viewed.

In some implementations, the chemical testing device is disposed in-line with the second fluid line.

In some implementations, the visual indicator includes a change in a color of the chemical testing device.

In some implementations, the substance includes leukocytes.

In some implementations, the substance includes nitrites.

In some implementations, the chemical testing device is a single-use device.

In some implementations, the chemical testing device is configured to detect the presence of the substance within the spent dialysate in real time.

In some implementations, the peritoneal dialysis fluid line set further includes a fluid hub configured to distribute fluid throughout the peritoneal dialysis fluid line set.

In some implementations, the fluid line is a first fluid line, and the peritoneal dialysis fluid line set further includes a second fluid line connected to the fluid hub and configured to deliver the spent dialysate from a patient to the fluid hub.

In some implementations, the fluid line is connected to the fluid hub and configured to deliver the spent dialysate from the fluid hub to the drain receptacle.

In another aspect, a PD system includes a PD fluid line set and a PD machine. The PD fluid line set includes a fluid line configured to carry spent dialysate to a drain receptacle and a chemical testing device disposed along the fluid line. The chemical testing device is configured to detect a presence of a substance in the spent dialysate as the spent dialysate flows past the chemical testing device, and the chemical testing device is configured to provide a visual indicator of the presence of the substance in the spent dialysate. The PD machine is configured to cooperate with the peritoneal dialysis fluid line set to pump the spent dialysate through the fluid line.

In another aspect, a method of detecting a presence of a substance in spent dialysate includes flowing the spent dialysate in a fluid line towards a drain receptacle and past a chemical testing device, detecting a presence of the substance in the spent dialysate at the chemical testing device, and providing, at the chemical testing device, a visual indicator of the presence of the substance within the spent dialysate.

Implementations may include one or more of the following features.

In some implementations, the chemical testing device includes a test pad that has an initial color and that includes one or more reagents that are reactive with the sub stance.

In some implementations, the chemical testing device further includes a control pad that lacks the one or more reagents and that has a reference color that is the same as the initial color of the test pad.

In some implementations, the method further includes contacting the substance with the one or more reagents and changing the initial color with respect to the reference color.

In some implementations, the substance is a first substance, and the method further includes detecting a presence of a second substance in the spent dialysate at the chemical testing device.

In some implementations, the method further includes passing the substance out of the spent dialysate and through a semi-permeable membrane of the chemical testing device.

In some implementations, the method further includes displaying the visual indicator at a lens of the chemical testing device.

In some implementations, providing the visual indicator of the presence of the substance within the spent dialysate includes changing a color of the chemical testing device.

In some implementations, the substance includes one or both of leukocytes and nitrites.

In some implementations, the method further includes detecting the presence of the substance in the spent dialysate in real time.

In some implementations, the fluid line is a first fluid line, and the method further includes flowing the spent dialysate in a second fluid line from a patient to a fluid hub and flowing the spent dialysate in the first fluid line from the fluid hub towards the drain receptacle and past the chemical testing device.

Implementations may provide one or more of the following advantages.

The chemical testing device can be a disposable, single-use device that is designed to be pre-installed to the drain line or connected to the drain line as an independent accessory device and to be discarded upon completion of a PD treatment. The chemical testing device can be a user-friendly, reliable device that provides real-time diagnosis of infection as effluent flows through the drain line. The chemical testing device can include, for example, fluid line connectors that permit easy installation of the testing device along the effluent flow path and can permit easy visual interpretation of test results. The chemical testing device can provide clear identification of infection within the effluent (e.g., as evidenced by non-ambiguous, distinct color changes of test pads), thereby eliminating ambiguity that may otherwise be encountered while examining effluent via other, conventional mechanisms, such as visual observation of a cloudy appearance of the effluent, which can be subjective and open to interpretation.

In many cases, a positive test result for substances (e.g., leukocytes and/or nitrites) detected by the chemical testing device provides an early-stage diagnosis of peritonitis (e.g., inflammation of the peritoneum). Such early-stage diagnosis provided by the chemical testing device can facilitate prompt treatment of peritonitis. Accordingly, the chemical testing device can be especially beneficial for patients with acute or chronic end-stage renal disease undergoing PD treatments in at home or in a healthcare facility.

Other aspects, features, and advantages will be apparent from the description, the drawings, and the claims.

DETAILED DESCRIPTION

Figure 1:
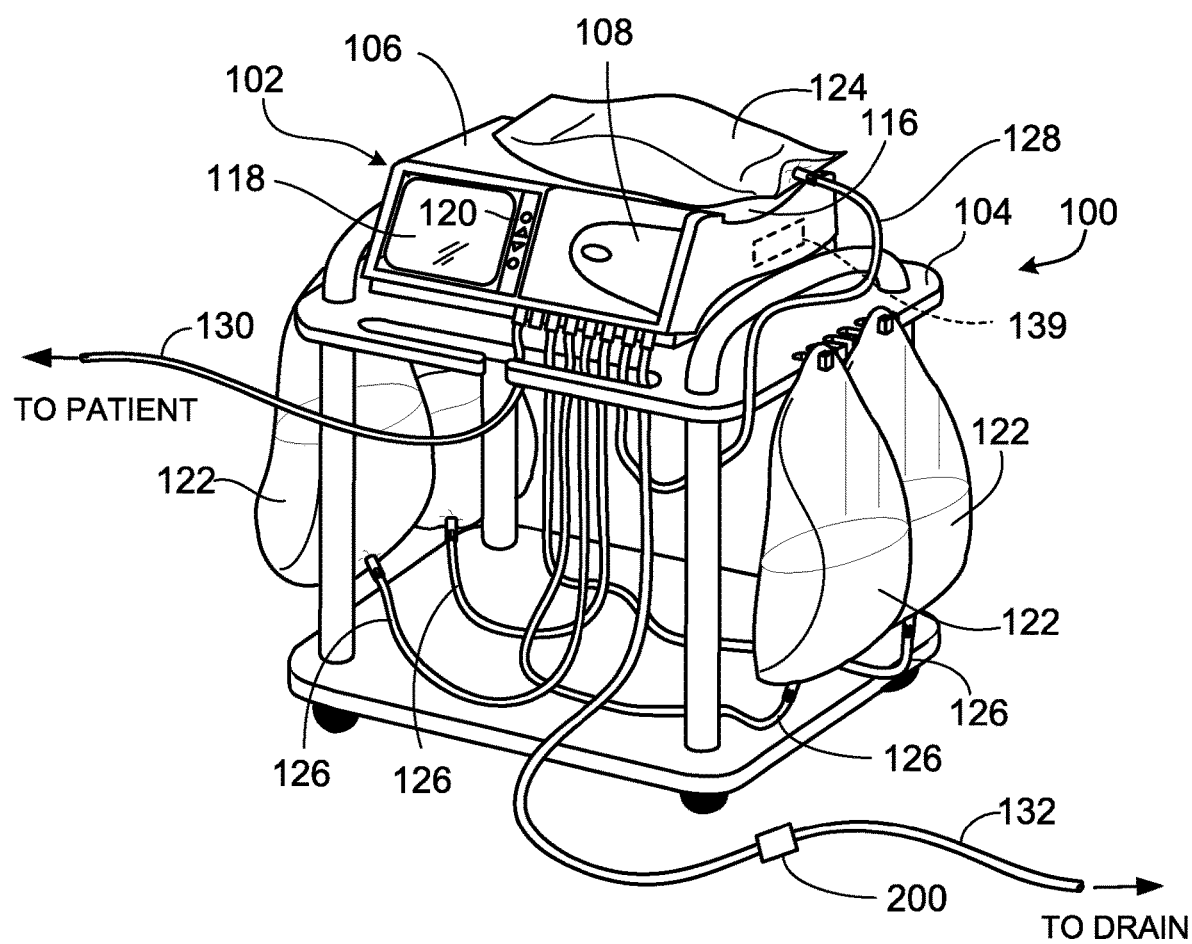
FIG. 1 is a perspective view of a peritoneal dialysis (PD) system that includes a chemical testing device positioned along a drain line of the PD system.
Figure 2:
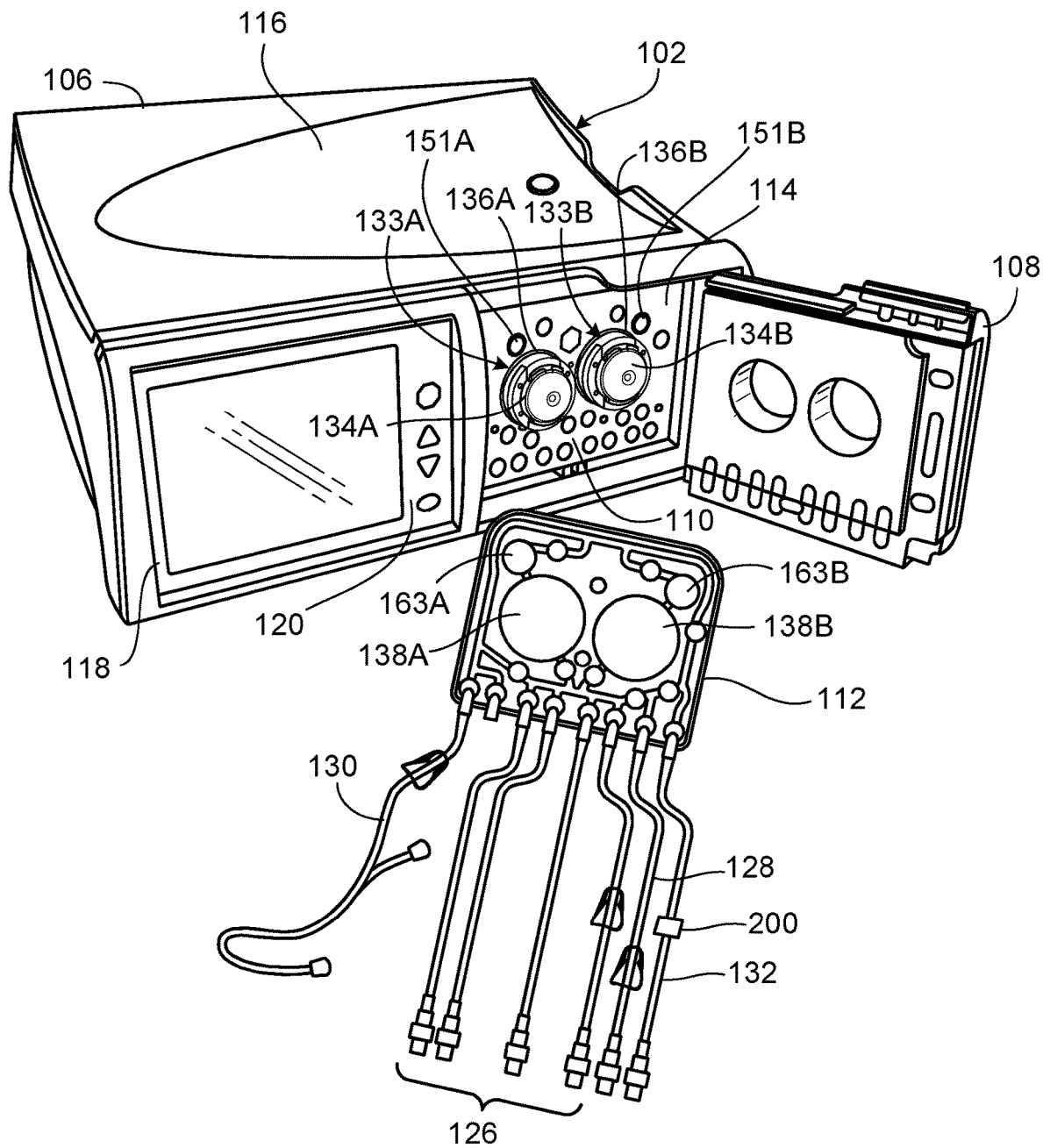
FIG. 2 is a perspective, exploded view of a PD cycler and a cassette of the PD system of FIG. 1.

A dialysis system (e.g., a peritoneal dialysis (PD) system) can include a chemical testing device (e.g., an infection tester) that is configured to provide an early indication of infection of a patient's peritoneum by analyzing spent dialysate flowing within fluid lines of the PD system from the patient to one or more drain bags or drain receptacles. Referring to FIG. 1, a PD system 100 includes a PD cycler 102 (also referred to as a PD machine) seated on a cart 104. Referring also to FIG. 2, the PD cycler 102 includes a housing 106, a door 108, and a cassette interface 110 that contacts a disposable PD cassette 112 when the cassette 112 is disposed within a cassette compartment 114 formed between the cassette interface 110 and the closed door 108. A heater tray 116 is positioned on top of the housing 106. The heater tray 116 is sized and shaped to accommodate a bag of dialysate (e.g., a 5 liter bag of dialysate). The PD cycler 102 also includes a touch screen 118 and additional control buttons 120 that can be operated by a user (e.g., a patient) to allow, for example, set-up, initiation, and/or termination of a PD treatment.

Dialysate bags 122 are suspended from fingers on the sides of the cart 104, and a heater bag 124 is positioned in the heater tray 116. The dialysate bags 122 and the heater bag 124 are connected to the cassette 112 via dialysate bag lines 126 and a heater bag line 128, respectively. The dialysate bag lines 126 can be used to pass dialysate from dialysate bags 122 to the cassette 112 during use, and the heater bag line 128 can be used to pass dialysate back and forth between the cassette 112 and the heater bag 124 during use. In addition, a patient line 130 and a drain line 132 are connected to the cassette 112. The patient line 130 can be connected to a patient's abdomen via a catheter and can be used to pass dialysate back and forth between the cassette 112 and the patient's peritoneal cavity during use. The drain line 132 can be connected to a drain or drain receptacle and can be used to pass spent dialysate (e.g., dialysate withdrawn from the patient's peritoneal cavity through the patient line 130) from the cassette 112 to the drain or drain receptacle during use. The spent dialysate is also referred to as effluent herein. The drain line 132 is equipped with a chemical testing device 200 that can be used to analyze the effluent to detect signs of infection of the patient's peritoneum, as will be discussed in more detail below with respect to FIGS. 4-9.

Figure 3:
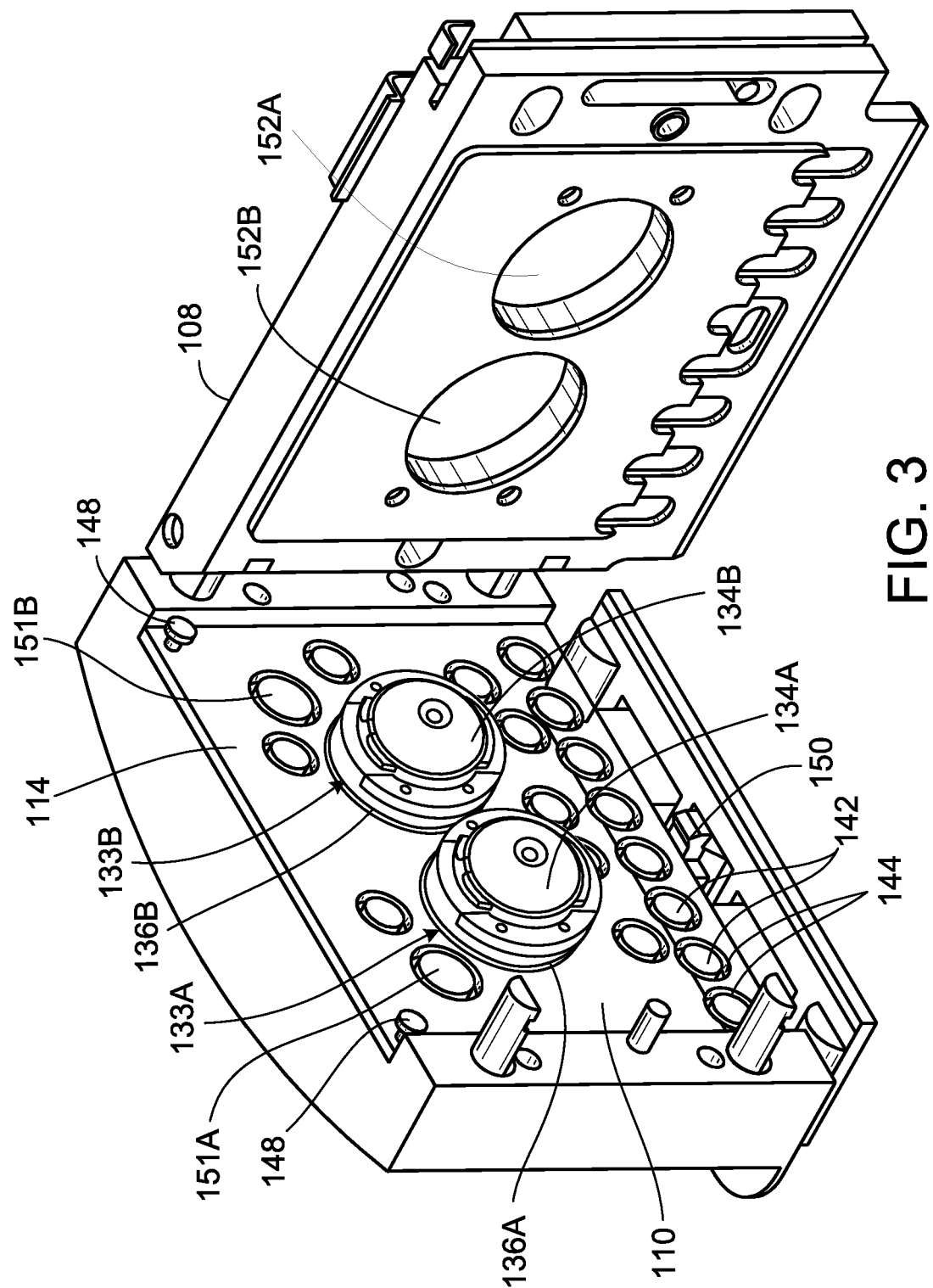
FIG. 3 is a perspective view of a cassette interface of the PD cycler of FIG. 2.

FIG. 3 shows a more detailed view of the cassette interface 110 and the door 108 of the PD cycler 102. As shown, the PD cycler 102 includes pistons 133A, 133B with piston heads 134A, 134B attached to piston shafts 135A, 135B (piston shaft 135A shown in FIG. 4) that can be axially moved within piston access ports 136A, 136B formed in the cassette interface 110. The piston shafts 135A, 135B are connected to stepper motors that can be operated to move the pistons 133A, 133B axially inward and outward such that the piston heads 134A, 134B move axially inward and outward within the piston access ports 136A, 136B. The stepper motors drive lead screws, which move nuts inward and outward along the lead screws. The nuts, in turn, are connected to the pistons 133A, 133B and thus cause the pistons 133A, 133B to move inward and outward as the stepper motors rotate the lead screws. Stepper motor controllers provide the necessary current to be driven through the windings of the stepper motors to move the pistons 133A, 133B. The polarity of the current determines whether the pistons 133A, 133B are advanced or retracted. In some implementations, the stepper motors require 200 steps to make a full rotation, and this corresponds to 0.048 inch of linear travel.

The PD system 100 also includes encoders (e.g., optical encoders) that measure the rotational movement of the lead screws. The axial positions of the pistons 133A, 133B can be determined based on the rotational movement of the lead screws, as determined by the encoders. Thus, the measurements of the encoders can be used to accurately position the piston heads 134A, 134B of the pistons 133A, 133B.

When the cassette 112 (shown in FIG. 2) is positioned within the cassette compartment 114 of the PD cycler 102 with the door 108 closed, the piston heads 134A, 134B of the PD cycler 102 align with pump chambers 138A, 138B of the cassette 112 such that the piston heads 134A, 134B can be mechanically connected to dome-shaped fastening members 161A, 161B of the cassette 112 overlying the pump chambers 138A, 138B. As a result of this arrangement, movement of the piston heads 134A, 134B toward the cassette 112 during treatment can decrease the volume of the pump chambers 138A, 138B and force dialysate out of the pump chambers 138A, 138B, while retraction of the piston heads 134A, 134B away from the cassette 112 can increase the volume of the pump chambers 138A, 138B and cause dialysate to be drawn into the pump chambers 138A, 138B.

As shown in FIG. 3, the cassette interface 110 includes two pressure sensors 151A, 151B that align with pressure sensing chambers 163A, 163B (shown in FIG. 2) of the cassette 112 when the cassette 112 is positioned within the cassette compartment 114. Portions of a membrane 140 of the cassette 112 that overlie the pressure sensing chambers 163A, 163B adhere to the pressure sensors 151A, 151B using vacuum pressure. Specifically, clearance around the pressure sensors 151A, 151B communicates vacuum to the portions of the cassette membrane 140 overlying the pressure sensing chambers 163A, 163B to hold those portions of the cassette membrane 140 tightly against the pressure sensors 151A, 151B. The pressure of fluid within the pressure sensing chambers 163A, 163B causes the portions of the cassette membrane 140 overlying the pressure sensing chambers 163A, 163B to contact and apply pressure to the pressure sensors 151A, 151B.

The pressure sensors 151A, 151B can be any sensors that are capable of sensing the fluid pressure in the sensing chambers 163A, 163B. In some implementations, the pressure sensors are solid state silicon diaphragm infusion pump force/pressure transducers. One example of such a sensor is the Model 1865 force/pressure transducer manufactured by Sensym Foxboro ICT. In certain implementations, the force/pressure transducer is modified to provide increased voltage output. The force/pressure transducer can, for example, be modified to produce an output signal of 0 to 5 volts.

Still referring to FIG. 3, the PD cycler 102 also includes multiple inflatable members 142 positioned within inflatable member ports 144 in the cassette interface 110. The inflatable members 142 align with depressible dome regions (not shown) of the cassette 112 when the cassette 112 is positioned within the cassette compartment 114 of the PD cycler 102. Dialysate can be pumped through the cassette 112 by actuating the piston heads 134A, 134B, and can be guided along desired flow paths within the cassette 112 by selectively inflating and deflating the various inflatable members 142.

Still referring to FIG. 3, locating pins 148 extend from the cassette interface 110 of the PD cycler 102. When the door 108 is in the open position, the cassette 112 can be loaded onto the cassette interface 110 by positioning the top portion of the cassette 112 under the locating pins 148 and pushing the bottom portion of the cassette 112 toward the cassette interface 110. The cassette 112 is dimensioned to remain securely positioned between the locating pins 148 and a spring loaded latch 150 extending from the cassette interface 110 to allow the door 108 to be closed over the cassette 112. The locating pins 148 help to ensure that proper alignment of the cassette 112 within the cassette compartment 114 is maintained during use.

The door 108 of the PD cycler 102, as shown in FIG. 3, defines cylindrical recesses 152A, 152B that substantially align with the pistons 133A, 133B when the door 108 is in the closed position. When the cassette 112 is positioned within the cassette compartment 114, hollow projections 154A, 154B of the cassette 112, inner surfaces of which partially define the pump chambers 138A, 138B, fit within the recesses 152A, 152B. The door 108 further includes a pad that is inflated during use to compress the cassette 112 between the door 108 and the cassette interface 110. With the pad inflated, the portions of the door 108 forming the recesses 152A, 152B support the projections 154A, 154B of the cassette 112 and the planar surface of the door 108 supports the other regions of the cassette 112. The door 108 can counteract the forces applied by the inflatable members 142 and thus allows the inflatable members 142 to actuate the depressible dome regions 146 on the cassette 112. The engagement between the door 108 and the hollow projections 154A, 154B of the cassette 112 can also help to hold the cassette 112 in a desired fixed position within the cassette compartment 114 to further ensure that the pistons 133A, 133B align with the fluid pump chambers 138A, 138B of the cassette 112.

A control unit 139 (e.g., a microprocessor, shown in FIG. 1) is connected to the pressure sensors 151A, 151B, to the stepper motors (e.g., the drivers of the stepper motors) that drive the pistons 133A, 133B, and to the encoders that monitor rotation of the lead screws of the stepper motors such that the control unit 139 can receive signals from and transmit signals to those components of the system. In some implementations, the control unit 139 is an MPC823 PowerPC device manufactured by Motorola, Inc. The control unit 139 monitors the components to which it is connected to determine whether any complications exists within the PD system 100. In the event of complications, the control unit 139 triggers one or more alarms which warn a patient or operator of the PD system 100 of conditions, e.g., conditions requiring attention from the patient or operator. The alarms can include audio alerts (e.g., generated by a speaker), visual alerts (e.g., displayed on touch screen 118), or other types of alerts.

Figure 4:
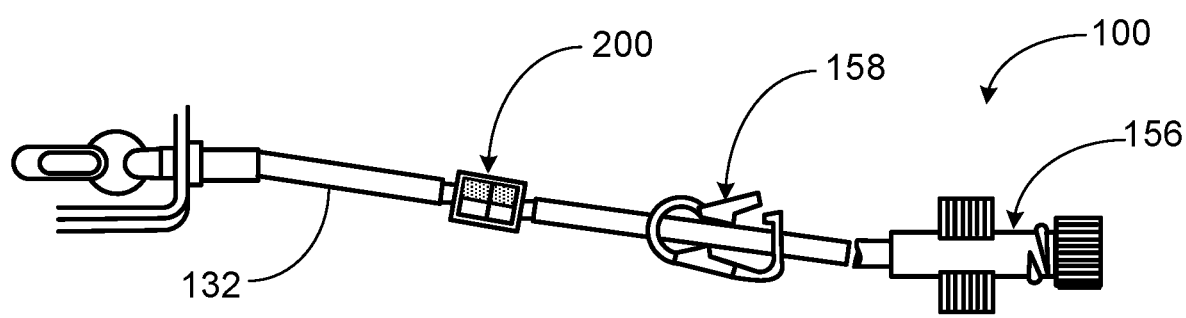
FIG. 4 is side view of a chemical testing device positioned along the drain line of the PD system of FIG. 1.

Referring to FIG. 4, the chemical testing device 200 (e.g., an infection tester) that is positioned along the drain line 132 is designed to provide one or more visual indications of infection within effluent flowing through the drain line 132. A connector 156 (e.g., a protective cap) is secured to a distal end of the drain line 132 for connecting the drain line 132 to one or more drain bags or for delivering the effluent to another drain receptacle, such as a bathtub, a toilet, or a sink. A clamp 158 is also attached to the drain line 132 for manually closing the drain line 132 upon completion of a treatment in order to prevent fluid leakage from the drain line 132.

Figure 5:
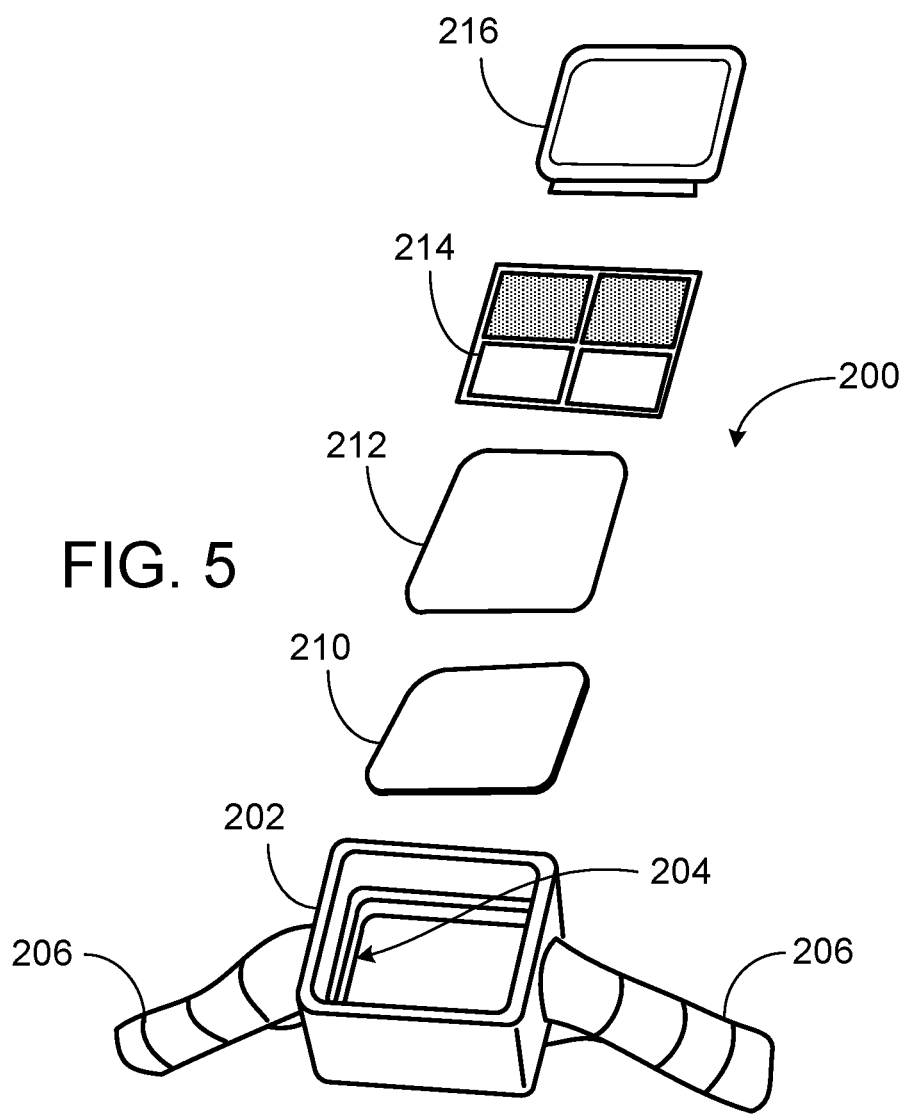
FIG. 5 is an exploded perspective view of the chemical testing device of FIG. 4.
Figure 6:
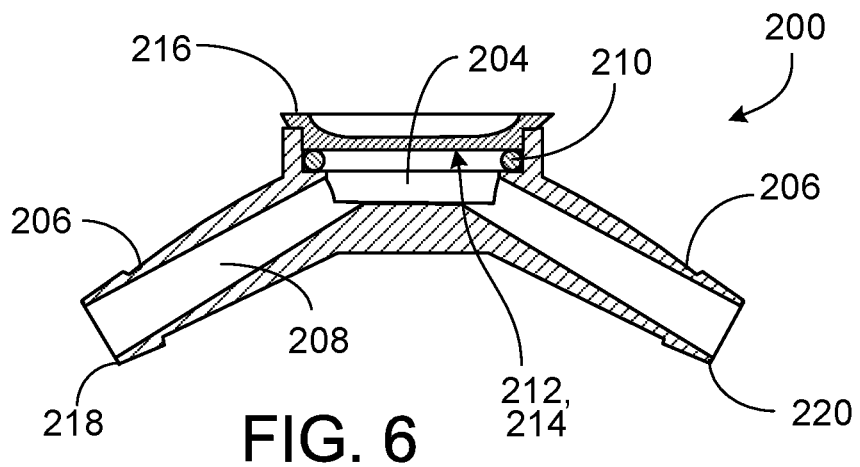
FIG. 6 is a cross-sectional view of the chemical testing device of FIG. 4.

Referring to FIGS. 5 and 6, the chemical testing device 200 includes a body 202 that defines a receptacle 204, two fluid line connectors 206, and a fluid channel 208 that extends from an end 218 of one fluid line connector 206, across the receptacle 204, and to an opposite end 220 of the other fluid line connector 206. The fluid line connectors 206 are sized and shaped to connect to the drain line 132 in a fluid-tight manner (e.g., via friction fit). The receptacle 204 typically has a length of about 1.8 cm to about 2.2 cm (e.g., about 2.0 cm) and a width of about 1.5 cm to about 1.9 cm (e.g., about 1.7 cm). The chemical testing device further includes a gasket 210, a membrane 212, a set of pads 214, and a lens 216 that seat within the receptacle 204. The gasket 210 (e.g., made of cure silicone) and the lens 216 together secure the membrane 212 and the set of pads 214 in position within the receptacle 204. The lens 216 is typically made of polycarbonate and provides a transparent window through which the set of pads 214 can be viewed by a user (e.g., the patient or a clinician). The lens 216 and the body 202 are typically made of one or more materials, including polycarbonate. The chemical testing device 200 typically has a total length of about 1.8 cm to about 2.2 cm (e.g., about 2.0 cm).

Figure 7:
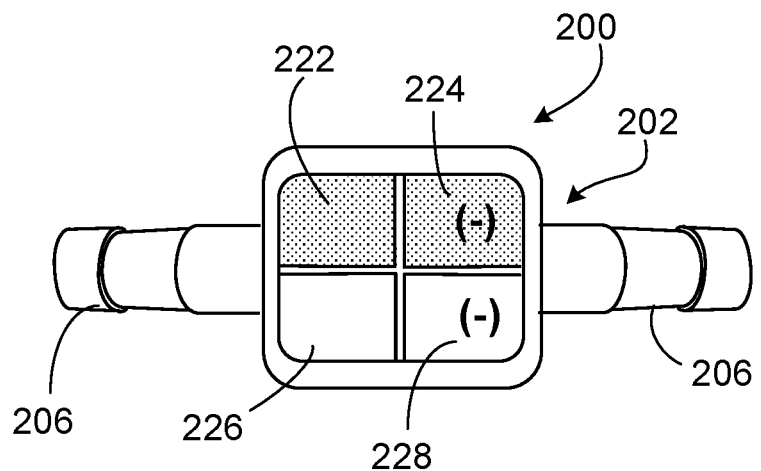
FIG. 7 is a top view of the chemical testing device of FIG. 4, showing negative test results.
Figure 8:
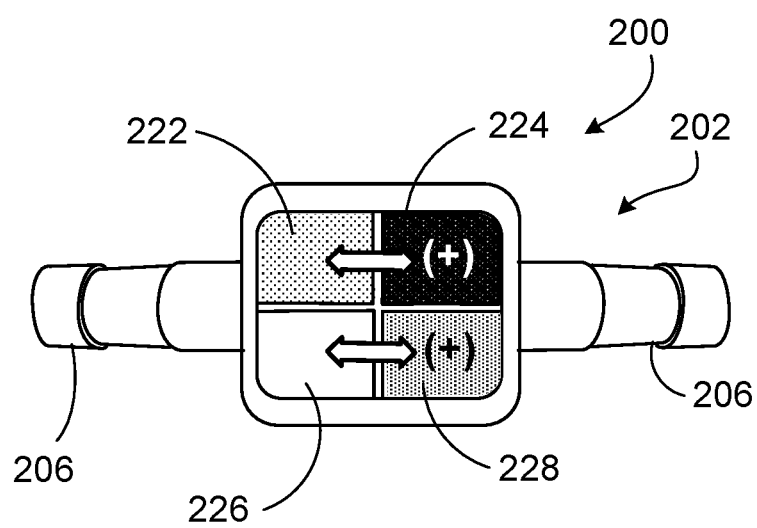
FIG. 8 is a top view of the chemical testing device of FIG. 4, showing positive test results.

Referring to FIGS. 6-8, the fluid channel 208 can allow passage of effluent from the cassette 112, past the receptacle 204, and to the one or more drain bags or drain receptacles. The membrane 212 is semi-permeable and has pores that are sized to allow passage of certain molecules. In some implementations, the pores have a width of about 0.19 µm to about 0.21 µm. Example molecules that can pass through the pores of the membrane 212 include leukocytes and nitrites, among other molecules (e.g., urobilinogen, various proteins, phenyl groups, hemoglobin, ketones, bilirubin, and glucose). The membrane 212 typically has a thickness of about 0.07 mm to about 0.09 mm and is typically made of one or more materials, including expanded polytetrafluoroethylene (ePTFE).

The set of pads 214 includes a control pad 222 for leukocytes (e.g., white blood cells), a test pad 224 for leukocytes, a control pad 226 for nitrites (e.g., nitrate-reducing bacteria), and a test pad 228 for nitrites. The test pads 224, 228 are formed as indicator papers and initially have colors that respectively match the colors of the control pads 222, 226. The test pad 224 includes reagents that cause the test pad 224 to change color within about 60 seconds to about 120 seconds of being contacted by a sufficient amount of leukocytes (e.g., upon the leukocytes being carried into the receptacle 204 within the effluent and crossing the membrane 212), whereas the control pad 222 lacks the reagents. For example, as shown in FIG. 8, when greater than or equal to a threshold amount of leukocytes contacts the test pad 224, the color of the test pad 224 changes (e.g., becomes darker or lighter) with respect to the color of the control pad 222, thereby indicating a positive test result. However, as shown in FIG. 7, when less than the threshold amount of leukocytes contacts the test pad 224, the color of the test pad 224 does not change color (e.g., remaining the same color as the control pad 222), thereby indicating a negative test result. Example reagents within the test pad 224 typically include indole carboxylic acid ester and diazonium salt, such that the test pad 224 can test for leukocyte esterase (LE), which is produced by neutrophils. LE is present within azurphilic granules monocytes and granulocytes, and a positive test result for LE typically indicates the presence of bacteria within the effluent. A positive test result for LE is also often associated with a positive test result for nitrites.

Similarly, the test pad 228 includes reagents that cause the test pad 228 to change color within about 60 seconds to about 120 seconds of being contacted by a sufficient amount of nitrites, whereas the control pad 226 lacks the reagents. For example, as shown in FIG. 8, when a threshold amount of nitrites contacts the test pad 228, the color of the test pad 228 changes (e.g., becomes darker or lighter) with respect to the color of the control pad 228, thereby indicating a positive test result. However, as shown in FIG. 7, when less than the threshold amount of nitrites contacts the test pad 228, the color of the test pad 228 does not change color (e.g., remaining the same color as the control pad 226), thereby indicating a negative test result. Example reagents within the test pad 228 typically include para-arsanilic acid and tetrahydrobenzoquinoline. Upon a patient observing a positive test result displayed by the chemical testing device 200, the patient can notify a medical professional of the test result.

The chemical testing device 200 can be a disposable, single-use device that is designed to be pre-installed to the drain line 132 or connected to the drain line 132 as an independent accessory device and to be discarded upon completion of a PD treatment. The chemical testing device 200 is a user-friendly, reliable device that provides real-time diagnosis of infection as effluent flows through the drain line 132. The chemical testing device 200 can advantageously provide clear identification of infection within the effluent (e.g., as evidenced by non-ambiguous, distinct color changes of the test pads 224, 228), thereby eliminating ambiguity that may otherwise be encountered while examining effluent via other, conventional mechanisms, such as visual observation of a cloudy appearance of the effluent, which can be subjective and open to interpretation. Other factors that can sometimes increase the difficulty in diagnosing peritonitis include the drainage of effluent directly into a toilet, a sink, or a bathtub (e.g., thereby making it difficult to see a cloudy appearance); a short dwell time in combination with a high volume, continuous dialysate flow, which would result in a lower leukocyte count and a less cloudy appearance; and a relatively dry peritoneal cavity during the daytime, which is typically associated with healthy individuals.

A positive test result for leukocytes and/or nitrites often provides an early-stage diagnosis of peritonitis (e.g., inflammation of the peritoneum). Such early-stage diagnosis provided by the chemical testing device 200 can facilitate prompt treatment of peritonitis. Accordingly, the chemical testing device 200 can be especially beneficial for patients with acute or chronic end-stage renal disease undergoing PD treatments in at home or in a healthcare facility.

Figure 9:
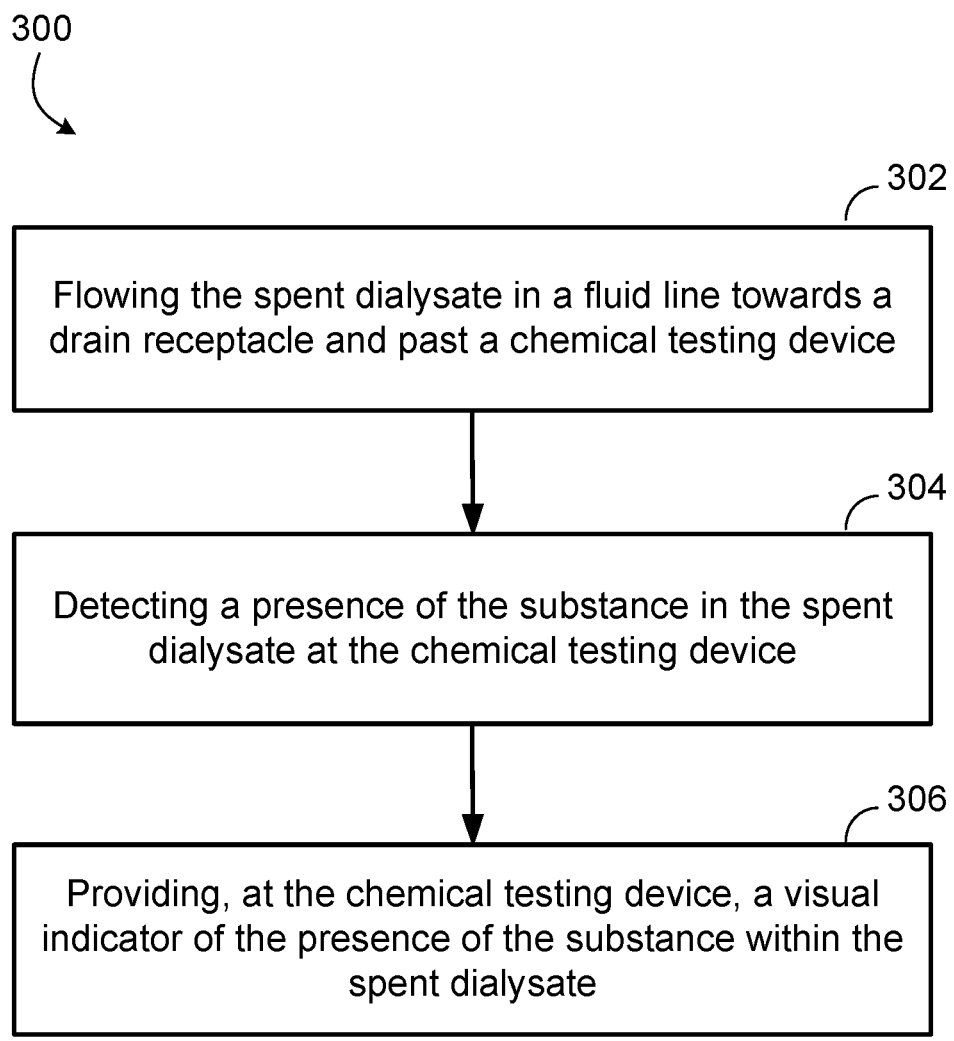
FIG. 9 is a flowchart showing a method of detecting a presence of a substance in spent dialysate using the PD system of FIG. 1, including the chemical testing device of FIG. 4.

FIG. 9 is a flowchart showing a method 300 of detecting a substance in spent dialysate during a PD treatment using the PD system 100, including the chemical testing device 200. In some implementations, the method 300 includes flowing the spent dialysate in a fluid line (e.g., the drain line 132) towards a drain receptacle and past a chemical testing device (e.g., the chemical testing device 200) (302). In some examples, the fluid line is a first fluid line, and the method further includes flowing the spent dialysate in a second fluid line from a patient to a fluid hub and flowing the spent dialysate in the first fluid line from the fluid hub towards the drain receptacle and past the chemical testing device.

In some implementations, the method 300 further includes detecting a presence of the substance (e.g., leukocytes and/or nitrites) in the spent dialysate at the chemical testing device (304). In some examples, the chemical testing device includes a test pad (e.g., the test pad 224, 228) that has an initial color and that includes one or more reagents that are reactive with the substance. In some examples, the chemical testing device further includes a control pad (e.g., the control pad 222, 226) that lacks the one or more reagents and that has a reference color that is the same as the initial color of the test pad. In some examples, the method further includes contacting the substance with the one or more reagents and changing the initial color with respect to the reference color. In some examples, the method further includes detecting a presence of a second substance in the spent dialysate at the chemical testing device. In some examples, the method further includes passing the substance out of the spent dialysate and through a semi-permeable membrane (e.g., the membrane 212) of the chemical testing device. In some examples, the method further includes detecting the presence of the substance in the spent dialysate in real time.

In some implementations, the method further includes providing, at the chemical testing device, a visual indicator of the presence of the substance within the spent dialysate (306). In some examples, providing the visual indicator of the presence of the substance within the spent dialysate includes changing a color of the chemical testing device (e.g., a color of a test pad 224, 228 of the chemical testing device). In some examples, the method further includes displaying the visual indicator at a lens (e.g., the lens 216) of the chemical testing device.

Figure 10:
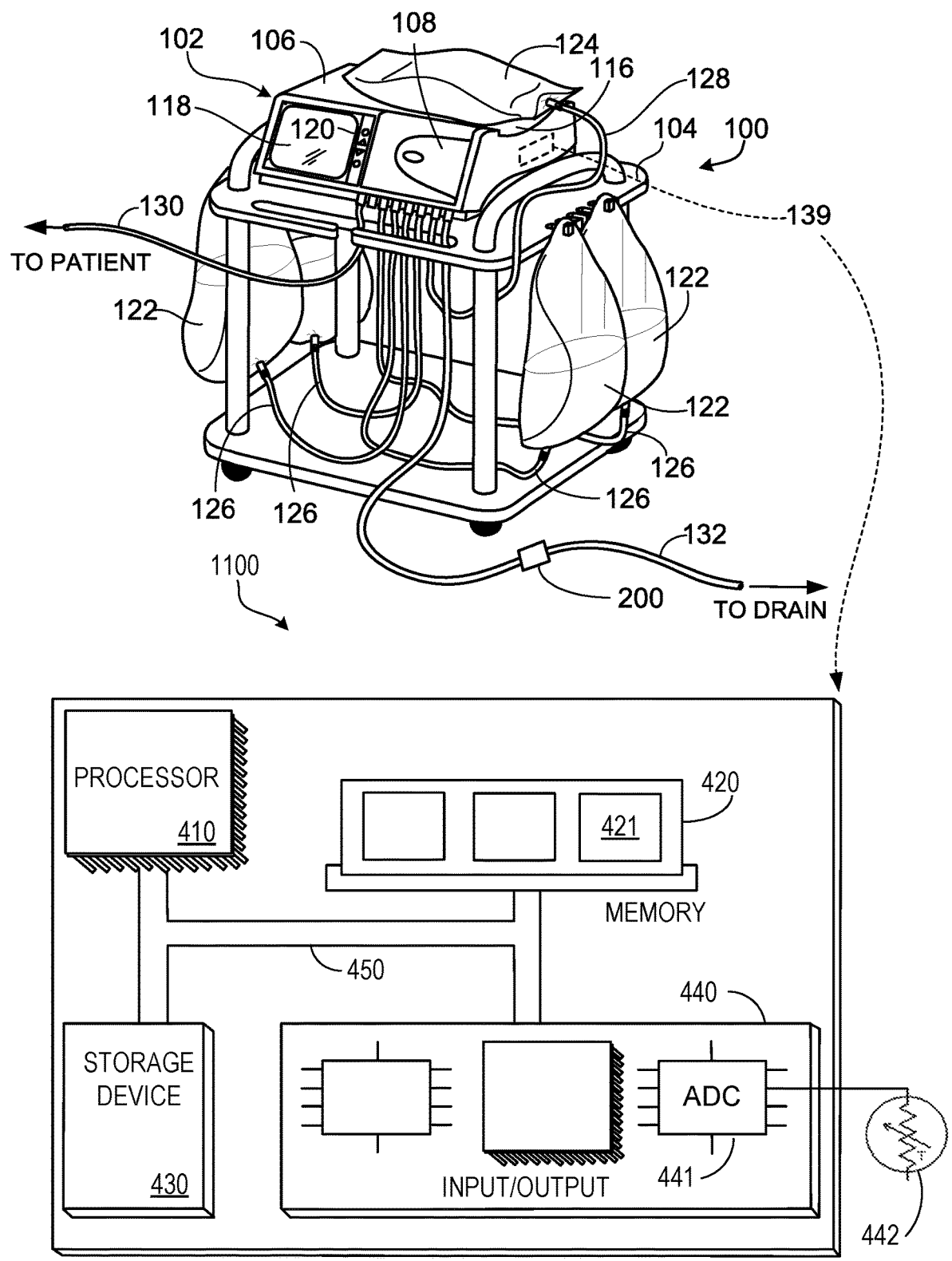
FIG. 10 is a block diagram of a control unit of the PD system of FIG. 1.

FIG. 10 is a block diagram of the control unit 139. The control unit 139 includes a processor 410, a memory 420, a storage device 430, and an input/output interface 440. Each of the components 410, 420, 430, and 440 can be interconnected, for example, using a system bus 450. The processor 410 is capable of processing instructions for execution within the control unit 139. The processor 410 can be a single-threaded processor, a multi-threaded processor, or a quantum computer. The processor 410 is capable of processing instructions stored in the memory 420 or on the storage device 430.

The memory 420 stores information within the control unit 139. In some implementations, the memory 420 is a computer-readable medium. The memory 420 can, for example, be a volatile memory unit or a non-volatile memory unit. The storage device 430 is capable of providing mass storage for the control unit 139. In some implementations, the storage device 430 is a non-transitory computer-readable medium. The storage device 430 can include, for example, a hard disk device, an optical disk device, a solid-date drive, a flash drive, magnetic tape, or some other large capacity storage device. The storage device 430 may alternatively be a cloud storage device, e.g., a logical storage device including multiple physical storage devices distributed on a network and accessed using a network.

The input/output interface 440 provides input/output operations for the control unit 139. In some implementations, the input/output interface 440 includes one or more of network interface devices (e.g., an Ethernet card), a serial communication device (e.g., an RS-232 10 port), and/or a wireless interface device (e.g., an 802.11 card, a 3G wireless modem, or a 4G wireless modem). In some implementations, the input/output device includes driver devices configured to receive input data and send output data to other input/output devices, e.g., keyboard, printer and display devices 118. In some implementations, mobile computing devices, mobile communication devices, and other devices are used.

In some implementations, the input/output interface 440 includes at least one analog-to-digital converter 441. An analog-to-digital converter converts analog signals to digital signals, e.g., digital signals suitable for processing by the processor 410. In some implementations, one or more sensing elements are in communication with the analog-to-digital converter 441, as will be discussed in more detail below.

In some implementations, the control unit 139 is a microcontroller. A microcontroller is a device that contains multiple elements of a computer system in a single electronics package. For example, the single electronics package could contain the processor 410, the memory 420, the storage device 430, and input/output interfaces 440.

Although an example processing system has been described in FIG. 10, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of nonvolatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of embodiments of the invention have been described. Nevertheless, it will be understood that various modifications may be made without departing from the spirit and scope of the invention. For example, while the PD system 100 has been described and illustrated as including a mechanical connection between the piston heads 134A, 134B and the cassette 112, in some embodiments, a PD system that is otherwise substantially similar in construction and function to the PD system 100 may include piston heads 134A, 134B and a cassette 112 that are secured to each other with a vacuum pressure instead of a mechanical connection. In such implementations, for example, the cassette interface can include annular openings that at least partially surround the piston heads 134A, 134B and are connected to a vacuum system that can be used to draw a vacuum on the cassette membrane 140 to secure the cassette membrane 140 to the piston heads 134A, 134B.

Figure 11:
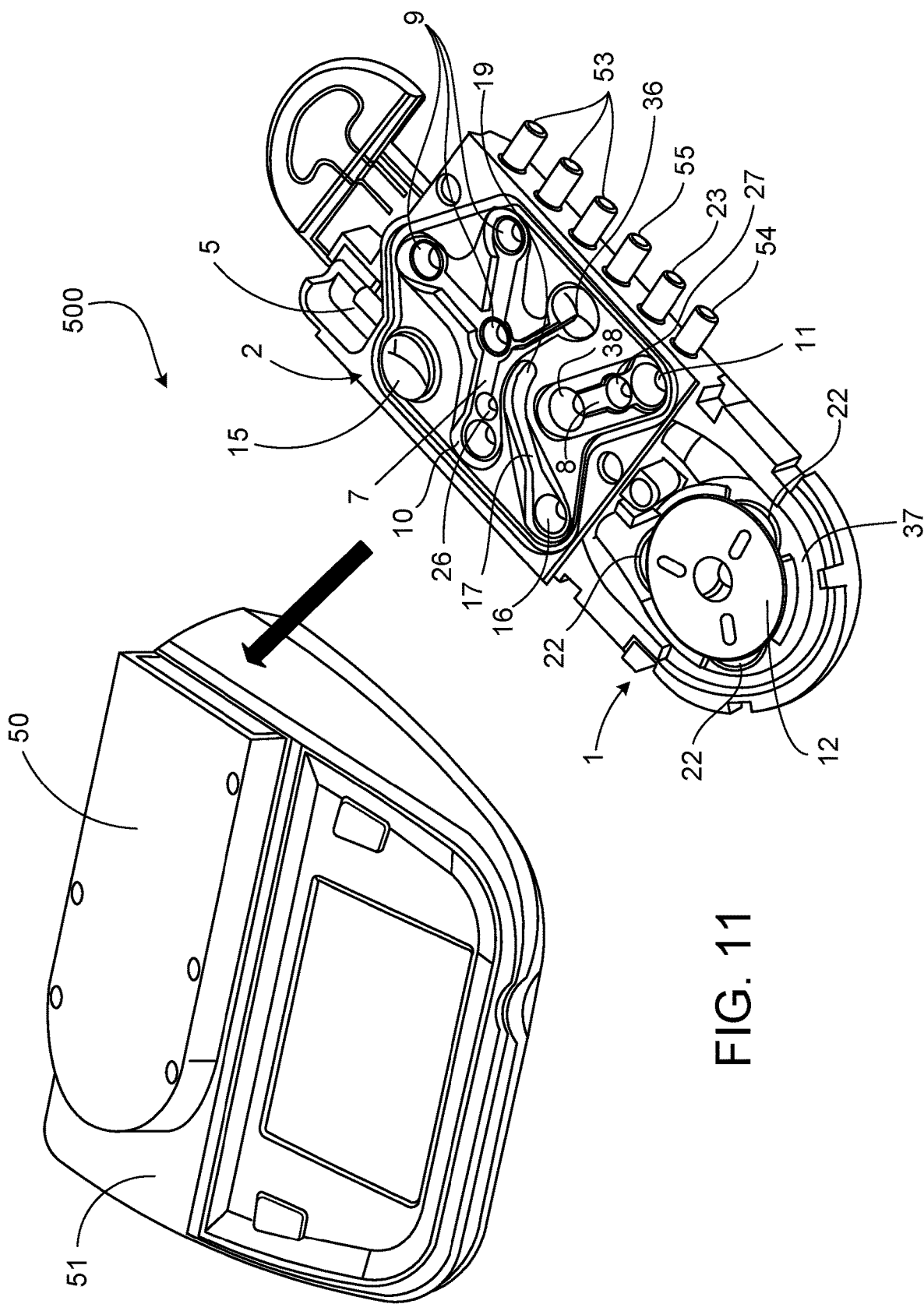
FIG. 11 is a perspective view of an alternative PD system that includes a PD cycler and a cartridge that, when connected to the PD cycler, forms a peristaltic pump.

While the PD system 100 has been described and illustrated as including piston pumps, in some embodiments, a PD system that is otherwise similar in construction and function to the PD system 100 may include one or more peristaltic pumps instead of piston pumps. FIG. 11, for example, illustrates a PD system 500 including a cycler 51 and a cartridge 2 (e.g., a liquid distribution system) that, when connected to the cycler 51, forms a peristaltic pump.

The cartridge 2 includes a pumping element 1, a first hub chamber 7, and a second hub chamber 8. The first chamber 7 includes a pump inlet 26 that can be connected to the pumping element 1 via a pump enter line, a liquid supply port 9 with a valve that can be connected to a liquid supply container via a liquid supply line, and a patient port 10 with a valve that can be connected to a patient via a patient line 5. The second hub chamber 8 includes a pump outlet 27 that can be connected to the pumping element 1 via a pump exit line, a drain port 11 with a valve that can be connected to a drain collector via a drain line along which a chemical testing device 200 positioned (e.g. as shown in FIG. 12), and a patient port 16 with a valve that can be connected to a patient 4 via the patient line 5.

The cartridge 2 further forms a cavity 15, which forms part of a pressure sensor. The first hub chamber 7 has three liquid supply ports 9, one patient port 10, one pump inlet 26, and a cavity 36 that forms part of a pressure sensor. The second hub chamber 8 has a patient port 18, a drain port 11, and a pump outlet 27. The cartridge 2 also includes a warmer chamber 17, which includes a warmer port 19 and a patient port 16. The warmer port 19 is connected to a warmer 28 (shown in FIG. 12) via a warmer tube connector 55 and a warmer exit line 30. The patient port 16 is connected to the patient line 5. The second hub chamber 8 includes a warmer port 38 connected to a warmer 28 via a warmer tube connector 23 and a warmer enter line 29.

The pumping element 1 includes a pump casing 45, which contains three rollers 22 maintained around a center of the pump casing 45 by a roller separator 12. The space between the roller separator 12 and the pump casing 45 defines a pump race 21 in which a flexible tube 37 is disposed. The flexible tube 37 is connected to the pump enter line 56 and the pump exit 57 line. The rollers 22 may be motor driven by a shaft 52 (shown in FIG. 13) in such a way as to progressively compress the flexible tube 37, thereby resulting in a peristaltic movement of fluid contained within and along the flexible tube 37. Accordingly, the pump casing 45, the rollers 22, the roller separator 12, and the pump race 21 together form a peristaltic pump by which liquid (e.g., dialysate) can be moved through the PD system 500.

Figure 12:
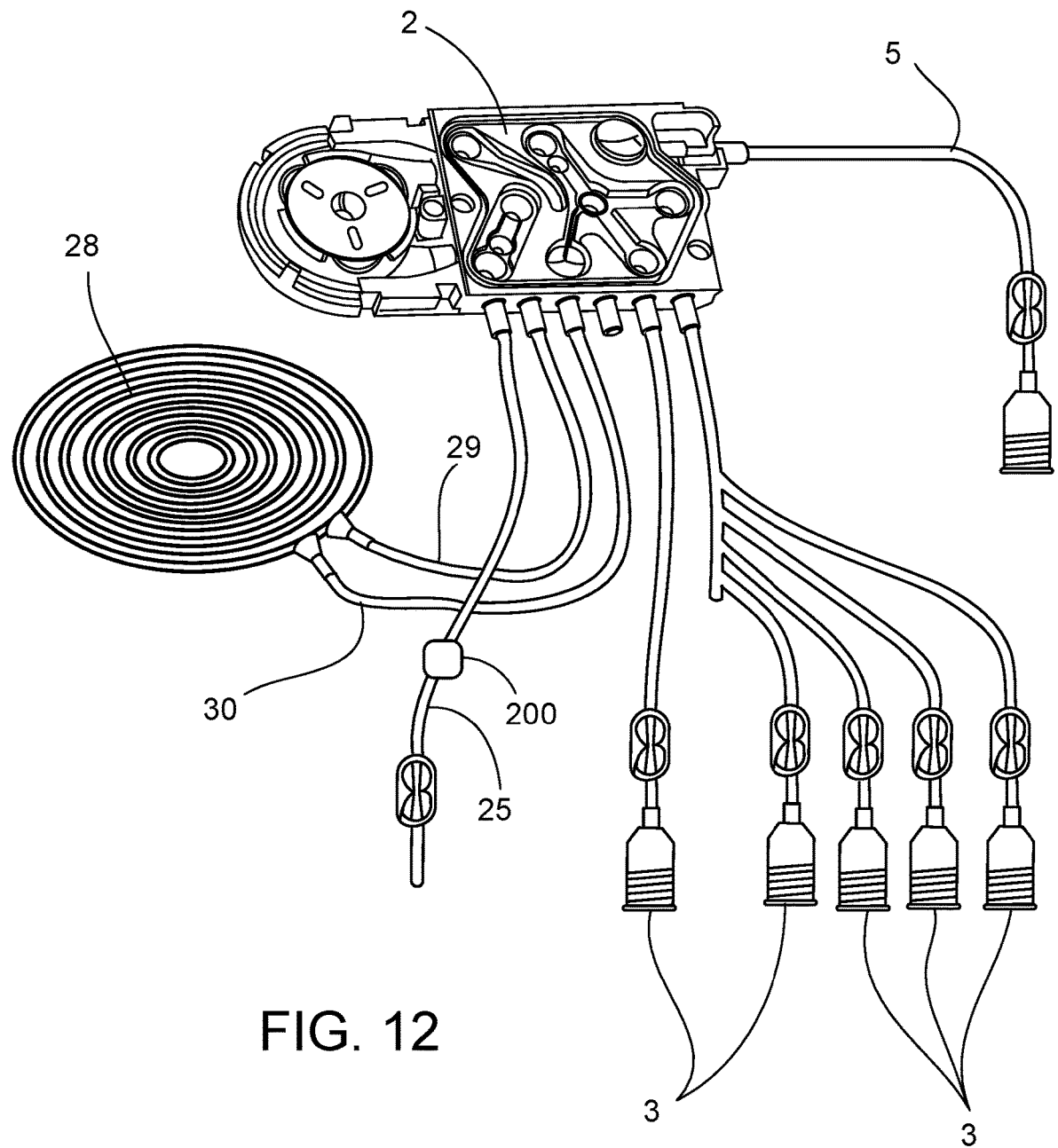
FIG. 12 is a perspective view of the cartridge of the PD system of FIG. 11, assembled with various fluid lines of the PD system of FIG. 11.

FIG. 12 shows an assembly including the cartridge 2, a patient line 5, supply bags 3, a warmer enter line 29, a warmer outer line 30, a warmer pouch 28 to be put into contact with a warming plate, a drain line 25, and the chemical testing device 25 installed to the drain line 25.

Figure 13:
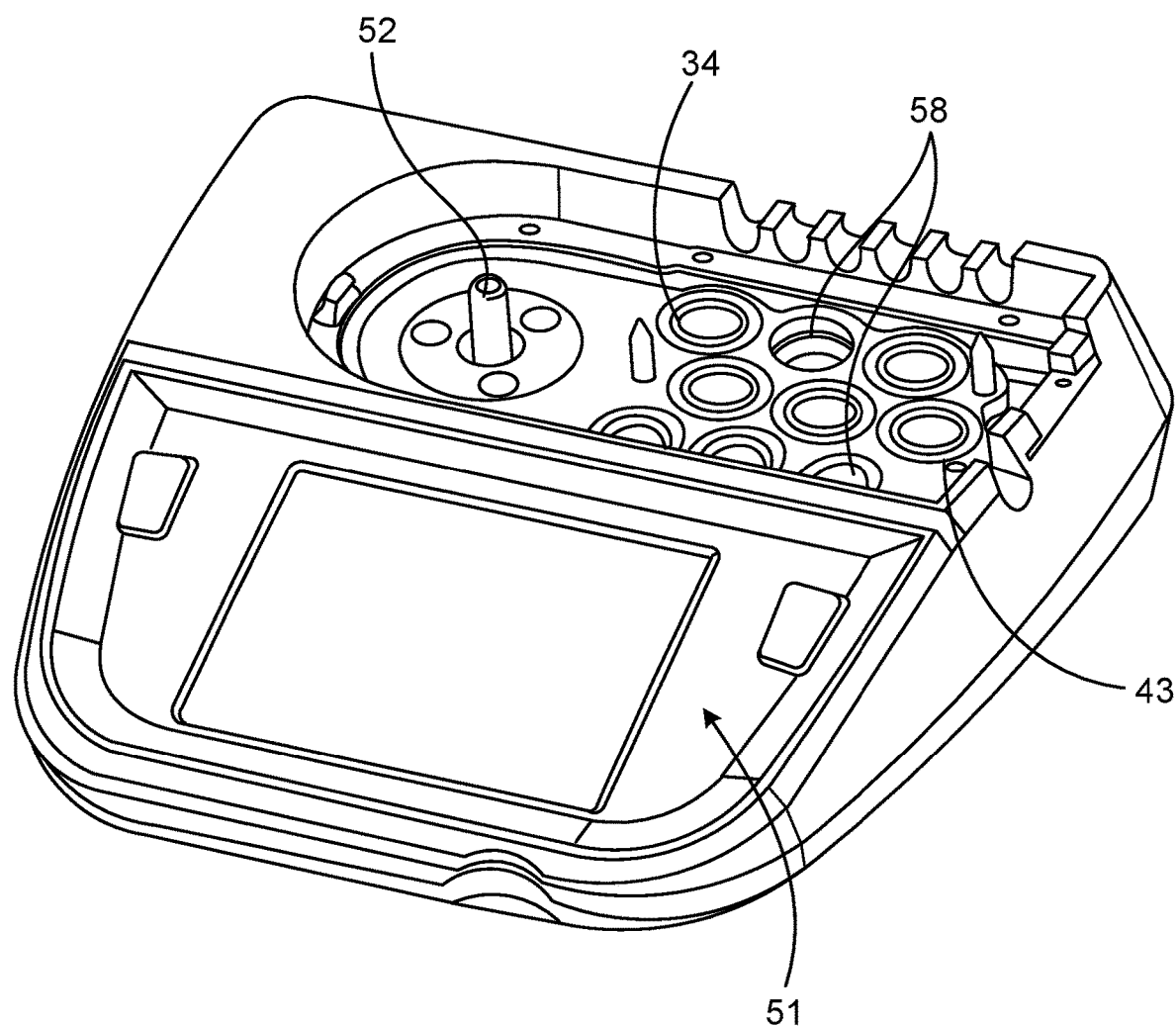
FIG. 13 is a perspective view of the PD cycler of the PD system of FIG. 11, with a cartridge slot of the PD cycler omitted.
Figure 14:
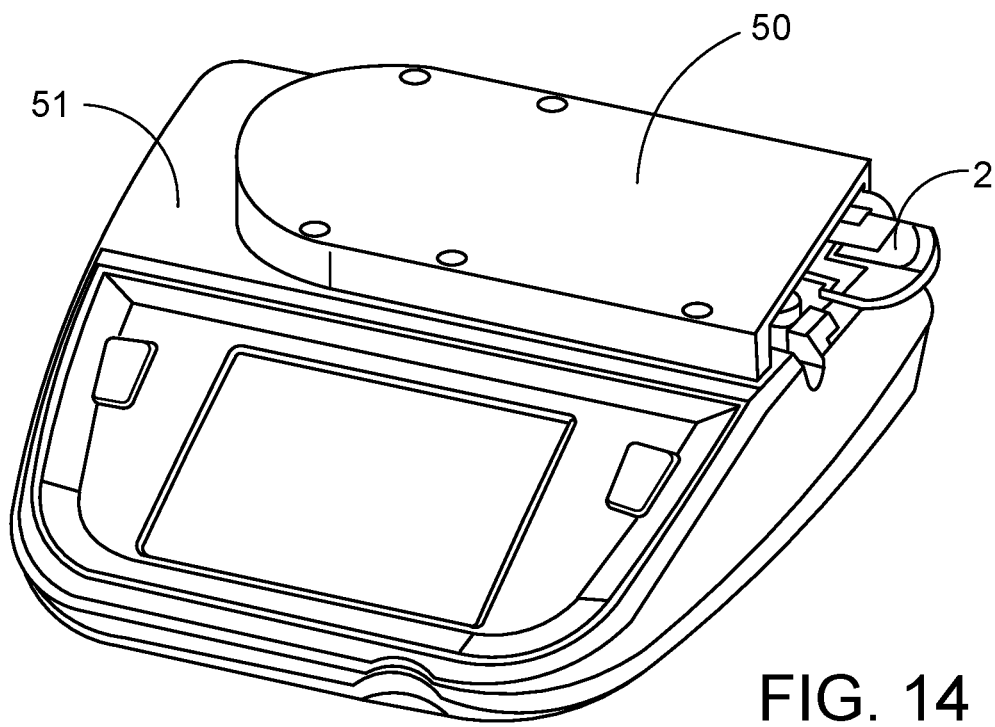
FIG. 14 is a perspective view of the PD cycler of FIG. 11 in an open configuration with the cartridge disposed therein.
Figure 15:
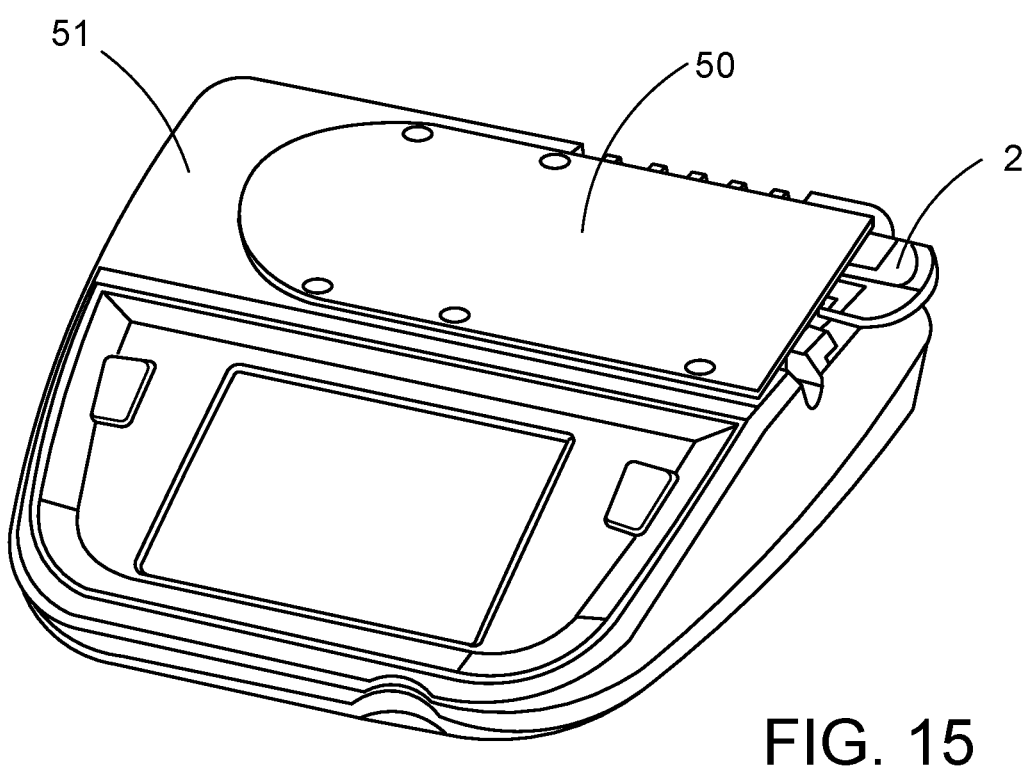
FIG. 15 is a perspective view of the PD cycler of FIG. 11 in a closed configuration with the cartridge disposed therein.

FIG. 13 shows the cycler 51 with the slot 50 and the cartridge 2 omitted to illustrate various internal features of the cycler 51. The cycler 51 includes a driving zone, which includes a several actuators 34 and a motor shaft 52 for interfacing with the rollers 22. The cycler 51 also includes an air sensor 43 situated close to the patient line 5 when the cartridge 2 is inserted. FIG. 14 shows the cycler 51 with the insertion slot 50 in an open configuration and with the cartridge 2 disposed within the insertion slot 50, while FIG. 15 shows the cycler 51 with the insertion slot 50 in a closed configuration and with the cartridge 2 disposed within the insertion slot 50.

While the cartridge 2 has been described and illustrated as including the pumping element 1, in some embodiments, the pumping element 1 and a remaining body of the cartridge 2 may be formed as separate components that are subsequently fixed together.

While methods of interpreting test results (e.g., a color change or a lack of color change of the test pads 224, 228 with respect to the control pads 222, 226) provided by the chemical infection tester 200 have been described as relying on visual observation by an individual (e.g., a patient or a medical practitioner) monitoring a dialysis treatment carried out by the PD systems 100, 500, in some embodiments, an automated mechanism can be used to interpret such test results. For example, in some embodiments, either of the PD systems 100, 500, can additionally include a reader that can be attached to the chemical testing device 200 (e.g., or to the drain line along which the chemical testing device 200 is positioned) to automatically detect a color change in the test pads 224, 228. In some embodiments, the reader is an optical sensor that is used to monitor the colors of the test pads 224, 228. In such embodiments, the control unit 139 can execute operations such as receiving one or more signals (e.g., indicating a positive test result from either or both of the test pads 224, 228) from the optical sensor and accordingly performing one or more actions, such as generating a notification (e.g., an indication of a positive test result) to be displayed on the touch screen 118.

While the components of the PD systems 100, 500 have been described and illustrated as having certain dimensions, shapes, and profiles, in some embodiments, a PD system that is otherwise substantially similar in construction and function to either of the PD systems 100, 500 may include one or more components that have one or more dimensions, shapes, or profiles that are different from those described above with respect to the PD systems 100, 500.

Other embodiments are within the scope of the following claims.

What is claimed is:

1. A peritoneal dialysis fluid line set, comprising:
a fluid line configured to carry spent dialysate to a drain receptacle and comprising a first portion and a second portion; and
a chemical testing device disposed between the first and second portions of the fluid line such that the first portion of the fluid line, the chemical testing device, and the second portion of the fluid line together define a bulk fluid flow path along which the spent dialysate flows in a bulk flow direction, the chemical testing device configured to detect a presence of a substance in the spent dialysate as the spent dialysate flows past the chemical testing device, the chemical testing device configured to provide a visual indicator of the presence of the substance in the spent dialysate, and the chemical testing device comprising:
a receptacle forming a portion of the bulk fluid flow path such that the spent dialysate flows through the receptacle in direct contact with the receptacle in the bulk flow direction;
a set of pads seated within the receptacle and comprising a test pad and a control pad that is separate from the test pad,
a semi-permeable membrane seated within the receptacle along the bulk fluid flow path such that the spent dialysate flows in direct contact with the membrane in the bulk flow direction, the semi-permeable membrane allowing passage of the substance from the spent dialysate to the set of pads, and
a lens seated within the receptacle and through which the set of pads are viewable for observance of the visual indicator, wherein each of the set of pads, the semi-permeable membrane, the lens, and the receptacle is oriented parallelly to the bulk flow path such that the spent dialysate continues to flow along the bulk flow direction as the visual indicator is viewed through the lens and as the spent dialysate flows through the receptacle of the chemical testing device.

2. The peritoneal dialysis fluid line set of claim 1, wherein the test pad that has an initial color and includes one or more reagents that are reactive with the sub stance.

3. The peritoneal dialysis fluid line set of claim 2, wherein the control pad lacks the one or more reagents and has a reference color that is the same as the initial color of the test pad.

4. The peritoneal dialysis fluid line set of claim 3, wherein the test pad is configured such that the initial color changes with respect to the reference color upon contact between the substance and the one or more reagents.

5. The peritoneal dialysis fluid line set of claim 3, wherein the substance is a first substance, the test pad is a first test pad, and the control pad is a first control pad, and wherein the set of pads further comprises a second test pad and a second control pad to detect a presence of a second substance in the spent dialysate as the spent dialysate flows past the chemical testing device, the second test pad and the second control pad being separate from each other and from the first test pad and the first control pad.

6. The peritoneal dialysis fluid line set of claim 5, wherein the initial reference colors of the first test pad and the first control pad are different from initial reference colors of the second test pad and the second control pad, respectively.

7. The peritoneal dialysis fluid line set of claim 1, wherein the chemical testing device is disposed in-line with the fluid line.

8. The peritoneal dialysis fluid line set of claim 1, wherein the visual indicator comprises a change in a color of the chemical testing device.

9. The peritoneal dialysis fluid line set of claim 1, wherein the substance comprises leukocytes.

10. The peritoneal dialysis fluid line set of claim 1, wherein the substance comprises nitrites.

11. The peritoneal dialysis fluid line set of claim 1, wherein the chemical testing device is a single-use device.

12. The peritoneal dialysis fluid line set of claim 1, wherein the chemical testing device is configured to detect the presence of the substance within the spent dialysate in real time.

13. The peritoneal dialysis fluid line set of claim 1, further comprising a fluid hub configured to distribute fluid throughout the peritoneal dialysis fluid line set.

14. The peritoneal dialysis fluid line set of claim 13, wherein the fluid line is a first fluid line, the peritoneal dialysis fluid line set further comprising a second fluid line connected to the fluid hub and configured to deliver the spent dialysate from a patient to the fluid hub.

15. The peritoneal dialysis fluid line set of claim 13, wherein the fluid line is connected to the fluid hub and configured to deliver the spent dialysate from the fluid hub to the drain receptacle.

16. A peritoneal dialysis system, comprising:
a peritoneal dialysis fluid line set, comprising:
a fluid line configured to carry spent dialysate to a drain receptacle and comprising a first portion and a second portion, and
a chemical testing device disposed between the first and second portions of the fluid line such that the first portion of the fluid line, the chemical testing device, and the second portion of the fluid line together define a bulk fluid flow path along which the spent dialysate flows in a bulk flow direction, the chemical testing device configured to detect a presence of a substance in the spent dialysate as the spent dialysate flows past the chemical testing device, the chemical testing device configured to provide a visual indicator of the presence of the substance in the spent dialysate, and the chemical testing device comprising:
- a receptacle forming a portion of the bulk fluid flow path such that the spent dialysate flows through the receptacle in direct contact with the receptacle in the bulk flow direction;
- a set of pads seated within the receptacle and comprising a test pad and a control pad that is separate from the test pad,
- a semi-permeable membrane seated within the receptacle along the bulk fluid flow path such that the spent dialysate flows in direct contact with the membrane in the bulk flow direction, the semi-permeable membrane allowing passage of the substance from the spent dialysate to the set of pads, and
- a lens seated within the receptacle and through which the set of pads are viewable for observance of the visual indicator, wherein each of the set of pads, the semi-permeable membrane, the lens, and the receptacle is oriented parallelly to the bulk flow path such that the spent dialysate continues to flow along the bulk flow direction as the visual indicator is viewed through the lens and as the spent dialysate flows through the receptacle of the chemical testing device; and a peritoneal dialysis machine configured to cooperate with the peritoneal dialysis fluid line set to pump the spent dialysate through the fluid line.

17. A method of detecting a substance in spent dialysate, the method comprising:

flowing the spent dialysate in a fluid line comprising a first portion and a second portion towards a drain receptacle and past a chemical testing device disposed between the first and second portions of the fluid line such that the first portion of the fluid line, the chemical testing device, and the second portion of the fluid line together define a bulk fluid flow path along which the spent dialysate flows in a bulk flow direction, the chemical testing device comprising:
- a receptacle forming a portion of the bulk fluid flow path such that the spent dialysate flows through the receptacle in direct contact with the receptacle in the bulk flow direction;
- a set of pads seated within the receptacle and comprising a test pad and a control pad that is separate from the test pad,
- a semi-permeable membrane seated within the receptacle along the bulk fluid flow path such that the spent dialysate flows in direct contact with the membrane in the bulk flow direction, the semi-permeable membrane allowing passage of the substance from the spent dialysate to the set of pads, and
- a lens seated within the receptacle and through which the set of pads are viewable, wherein each of the set of pads, the semi-permeable membrane, the lens, and the receptacle is oriented parallelly to the bulk flow path such that the spent dialysate continues to flow along the bulk flow direction as the visual indicator is viewed through the lens and as the spent dialysate flows through the receptacle of the chemical testing device;

detecting a presence of the substance in the spent dialysate at the set of pads of the chemical testing device; and displaying, at the set of pads of the chemical testing device, a visual indicator of the presence of the substance within the spent dialysate through the lens of the chemical testing device.

18. The method of claim 17, wherein the test pad has an initial color and includes one or more reagents that are reactive with the substance.

19. The method of claim 18, wherein the control pad lacks the one or more reagents and has a reference color that is the same as the initial color of the test pad.

20. The method of claim 19, further comprising:
contacting the substance with the one or more reagents; and
changing the initial color with respect to the reference color.

21. The method of claim 19, wherein the substance is a first substance, the method further comprising detecting a presence of a second substance in the spent dialysate at the chemical testing device.

22. The method of claim 17, further comprising passing the substance out of the spent dialysate and through the semi-permeable membrane of the chemical testing device.

23. The method of claim 17, wherein displaying the visual indicator of the presence of the substance within the spent dialysate comprises changing a color of the chemical testing device.

24. The method of claim 17, wherein the substance comprises one or both of leukocytes and nitrites.

25. The method of claim 17, further comprising detecting the presence of the substance in the spent dialysate in real time.

26. The method of claim 17, wherein the fluid line is a first fluid line, the method further comprising:
flowing the spent dialysate in a second fluid line from a patient to a fluid hub; and
flowing the spent dialysate in the first fluid line from the fluid hub towards the drain receptacle and past the chemical testing device.

27. The peritoneal dialysis fluid line set of claim 1, wherein the semi-permeable membrane, the set of pads, and the lens are positioned serially along a direction that is perpendicular to the bulk flow direction.

28. The peritoneal dialysis fluid line set of claim 1, wherein the substance flows towards the set of pads in a direction that is perpendicular to the bulk flow direction of the spent dialysate.

29. The peritoneal dialysis fluid line set of claim 5, wherein the first test pad, the first control pad, the second test pad, and the second control pad are positioned in a 2×2 matrix arrangement.

* * * * *

UNITED STATES PATENT AND TRADEMARK OFFICE
CERTIFICATE OF CORRECTION

| | | |
|---|---|---|
| PATENT NO. | : 11,255,844 B2 | Page 1 of 1 |
| APPLICATION NO. | : 15/912874 | |
| DATED | : February 22, 2022 | |
| INVENTOR(S) | : Diego Suarez del Real Pena and Irving Uziel Hernandez | |

It is certified that error appears in the above-identified patent and that said Letters Patent is hereby corrected as shown below:

In the Claims

Column 14, Line 7, in Claim 2, delete "sub stance." and insert --substance.--.

Signed and Sealed this
Twenty-fourth Day of May, 2022

*Katherine Kelly Vidal*

Katherine Kelly Vidal
*Director of the United States Patent and Trademark Office*